United States Patent [19]
Horowitz et al.

[11] Patent Number: 5,697,100
[45] Date of Patent: Dec. 16, 1997

[54] NOSE AND CHEEK WARMER AND PROTECTOR

[76] Inventors: Marion Horowitz, 180 Chestnut Dr.; Cheryl Brayman, 150 Birch Dr., both of Roslyn, N.Y. 11576

[21] Appl. No.: 686,668

[22] Filed: Jul. 26, 1996

[51] Int. Cl.$^6$ .................... A41D 13/00; A61F 9/02
[52] U.S. Cl. .................... 2/9; 2/13; 2/427
[58] Field of Search .................... 2/13, 427, 9, 206, 2/15, 424, 909, 439, 429; 602/74; 128/857, 858; 351/138, 123, 158

[56] References Cited

U.S. PATENT DOCUMENTS

| | | | |
|---|---|---|---|
| 1,020,994 | 3/1912 | Leasure | 2/427 |
| 1,035,217 | 8/1912 | McQuary | 2/427 |
| 1,097,538 | 5/1914 | Cordova | 2/427 |
| 1,279,884 | 9/1918 | LaRoche | 2/427 |
| 1,585,023 | 5/1926 | Fant | 2/13 |
| 2,197,973 | 4/1940 | Everett et al. | 2/13 |
| 2,519,561 | 8/1950 | Gillman et al. | 2/13 |
| 2,669,717 | 2/1954 | Diggs | 2/427 |
| 3,768,100 | 10/1973 | Colman et al. | 2/206 |
| 4,250,577 | 2/1981 | Smith | 2/9 |
| 4,653,124 | 3/1987 | McNeal et al. | 2/427 |
| 4,797,956 | 1/1989 | Boyce | 2/13 |
| 5,020,533 | 6/1991 | Hubbard et al. | 2/427 |
| 5,033,128 | 7/1991 | Torres | 2/427 |
| 5,220,689 | 6/1993 | Miller | 2/427 |
| 5,416,923 | 5/1995 | Peugh | 2/206 |
| 5,438,710 | 8/1995 | McDonald | 2/9 |
| 5,553,321 | 9/1996 | Cassel | 2/13 |
| 5,592,687 | 1/1997 | Lajeunesse | 2/9 |
| 5,619,750 | 4/1997 | Allewalt | 2/13 |

Primary Examiner—Amy B. Vanatta

[57] ABSTRACT

The nose and cheek warmer and protector is to be used by skiers as an attachment to ski goggles. It consists of an opaque, thermally insulating and absorptive material which helps to keep the skin surface in the areas surrounding the lower part of the eyes, the nose, and the upper cheeks warm, reduces windburn, reduces sunburn, and reduces moisture accumulation from perspiration or the weather elements. It is attached by means of the hook type of fasteners by a skier to ski goggles to provide maximum comfort and protection. It can be laundered.

1 Claim, 3 Drawing Sheets

NOSE AND CHEEK WARMER AND PROTECTOR

BACKGROUND

1. Field of Invention

This invention relates to facial coverings, specifically to those coverings which attach to ski goggles to minimize heat loss.

2. Background of the Invention

Alpine skiing is a very popular recreational sport which many people participate in throughout the world. In recent years snowboarding and snowmobiling have increased the numbers of people participating in outdoor winter sports. Unfortunately, every season there are many injuries which these participants can sustain, including broken bones due to falls and/or collisions as well as various problems resulting from exposure to the elements. The cold temperatures, in addition to the wind battering the body, can create physical difficulties for the skier during the ascent to the top of the mountain or the descent to the bottom. The part of the body which is the most adversely affected by the temperature and wind is the most exposed portion of the body which is the face. Many skiers have suffered from frostbite and/or windburn of the upper cheeks and nose as a result of weather conditions. Them is also the problem of increased cooling of the exposed skin due to heat loss through the heat of evaporation when perspiration or moisture from the snow on the skin surface evaporates, thereby increasing the rate at which heat is lost from the skin surface. Wind conditions can increase the rate of evaporation, thereby increasing the rate at which heat is lost from the skin surface. On some very sunny days, there is also the possibility of sunburn to the upper cheeks and nose. All these factors which adversely affect the participant, reduce the enjoyment of the sport and can potentially create a harmful medical condition.

Many skiers wear goggles to protect their eyes from snow, debris, wind, or as a cover for prescription lenses. This would still leave the majority of the face exposed. Various face coverings have been used by many skiers in an attempt to protect their skin from exposure. Face coverings that are generally used fall into two broad categories. There are the hood type that go over the entire head. There are apertures for the eyes and they may or may not have apertures for the nose and mouth. The other type of face covering goes over the entire face with some means of attaching the covering to the head around the back of the head or to goggles. This type of covering also has apertures for the eyes and may or may not have apertures for the nose and mouth. However, there is no means to adjust these coverings to the different sizes which exist due to peoples' varying head sizes as well as an individual's varying facial dimensions and proportions. Many skiers do not fit comfortably into these coverings. The hood type may be too small or too large to fit properly and the various apertures may not be in the correct position for a particular person. For example, the distance between the eyes may not be correct and the distance between the openings for the eyes and the distance to the nose and/or mouth may not be correct. In addition, there can be some restriction in comfortable lateral and vertical moving of the head if the covering is not flexible enough to "give" in the direction of motion. Currently, there is no means to solve all the aforementioned problems which afford the skier maximum comfort to enjoy the sport and minimize some of the medical difficulties which may arise.

OBJECTS AND ADVANTAGES OF THE INVENTION

1. To provide skiers with varying facial dimensions and proportions a thermally insulating device which can be readily molded to fit their particular faces.

2. To provide the skier with a device which will be adaptable to the majority of ski goggles which are currently commercially available, even after continued usage and/or launderings.

3. To reduce the possibility of frostbite and heat loss from the skin surface due to moisture evaporation around the eyes, upper cheeks and nose.

4. To reduce the accumulation of moisture inside the ski goggles thereby keeping the goggle surface dryer and clearer for vision.

5. To reduce the possibility of windburn to the nose and upper cheeks.

6. To reduce the possibility of sunburn to the upper cheeks and nose.

GENERAL DESCRIPTION OF THE DRAWINGS

DETAILED DESCRIPTION OF THE DRAWINGS

Figure 1:
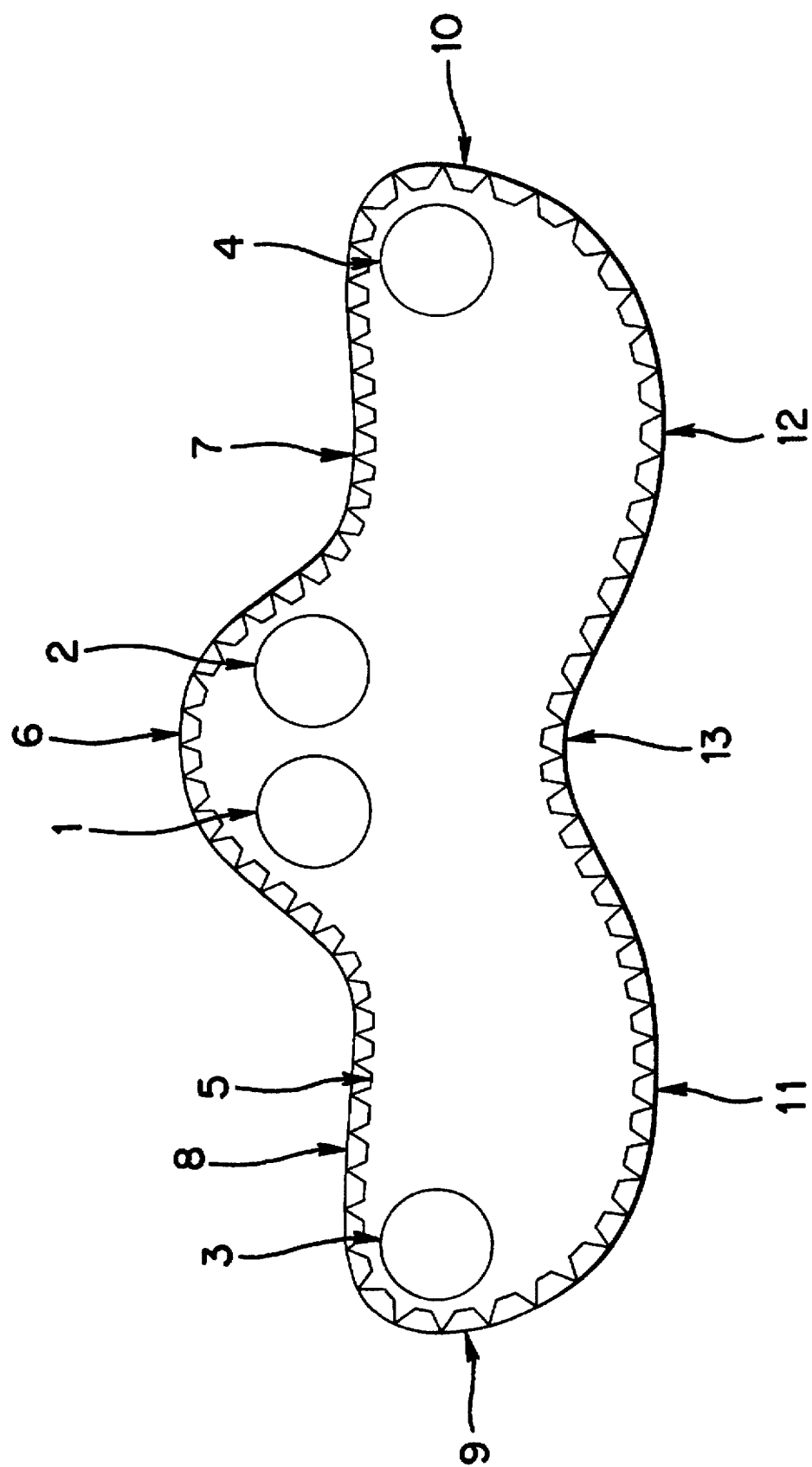
FIG. 1 is a top view of the invention which attaches to the under surface of ski goggles.

The general shape of the invention allows for a form fitting nose and cheek warmer and protector to conform to the contours of a person's particular features. In FIG. 1, the panel which forms the nose and cheek warmer is illustrated, having a perimeter which consists of areas 6, 7, 8, 9, 10, 11, 12, and 13. The perimeter has a top edge area, 6, which lies against the skin over the bridge of the nose, and areas 7 and 8 which lie against the skin below the eye area. The areas 9 and 10 comprise the edge which lies against the skin of the upper cheek area parallel to the vertical plane of the face. The lower edge of the perimeter consists of areas 11 and 12 which lie against the skin along the upper cheek area, and area 13 which lies against the skin of the lower tip of the nose above the nostril area; it does not extend past the tip of the nose. In FIG. 1, the hook portion of the hook and loop type of fasteners are located in positions 1, 2, 3, and 4. These hook type fasteners attach to the foam lining of ski goggles and can be adjusted in their placement on the foam lining by the individual for maxima contact with the skin and for maximum comfort. Fasteners 1 and 2 attach to the foam on either side of the nose. Fasteners 3 and 4 attach to the foam on the outer curve of the goggles, along the upper curve of the cheek area. In FIG. 1, the outer edge of the invention, section 5, is sewn over with any durable sewing thread. The stitch pattern is functional and decorative. This stitching has thread which runs parallel to the perimeter, as well as going from the upper surface (surface 1, FIG. 2), over and around the edge to the lower surface (surface 2, FIG. 2), thereby enclosing the perimeter edge in thread. The stitching helps to maintain the integrity of the shape of the invention, while reducing the amount of fraying of the material which might occur after continued usage and/or launderings. The particular stitch pattern may vary, as long as it conforms to the objects and advantages of the invention.

Figure 2:
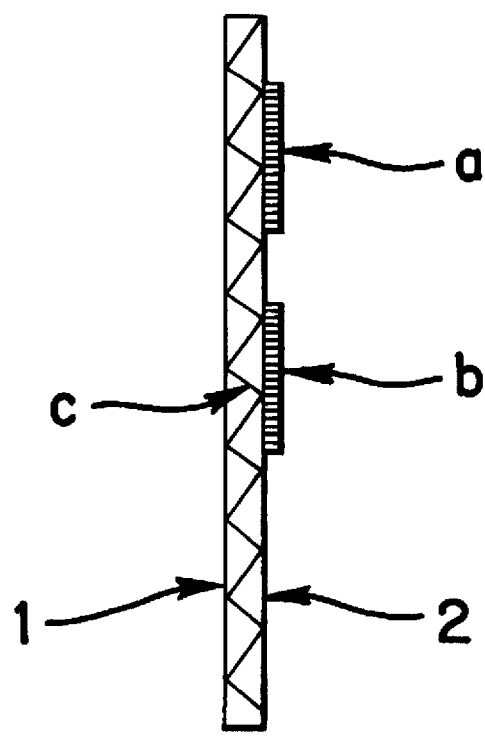
FIG. 2 is a lateral view of the invention.

A single layer of thermally insulated opaque material with absorptive properties is used for this invention. FIG. 2 illustrates the lateral view of the invention. Surface 1 is the side that makes contact with the surface of the skin. A suitable type of material to be used is fleece, but other materials providing the same advantages as stated in the objects and advantages of the invention might also be used. It is opaque, thereby not allowing the sun to make direct contact with the skin. It is thermally insulating, thereby keeping the skin surface warmer addition to providing a physical barrier to the weather elements. Surface 2 is the surface that makes contact with the foam lining of the goggles. On surface 2, the lateral view of the hook fasteners a and b are shown. The lateral view of the thread over the edge of the invention, going from surface 1 to surface 2 is illustrated by c.

Figure 3:
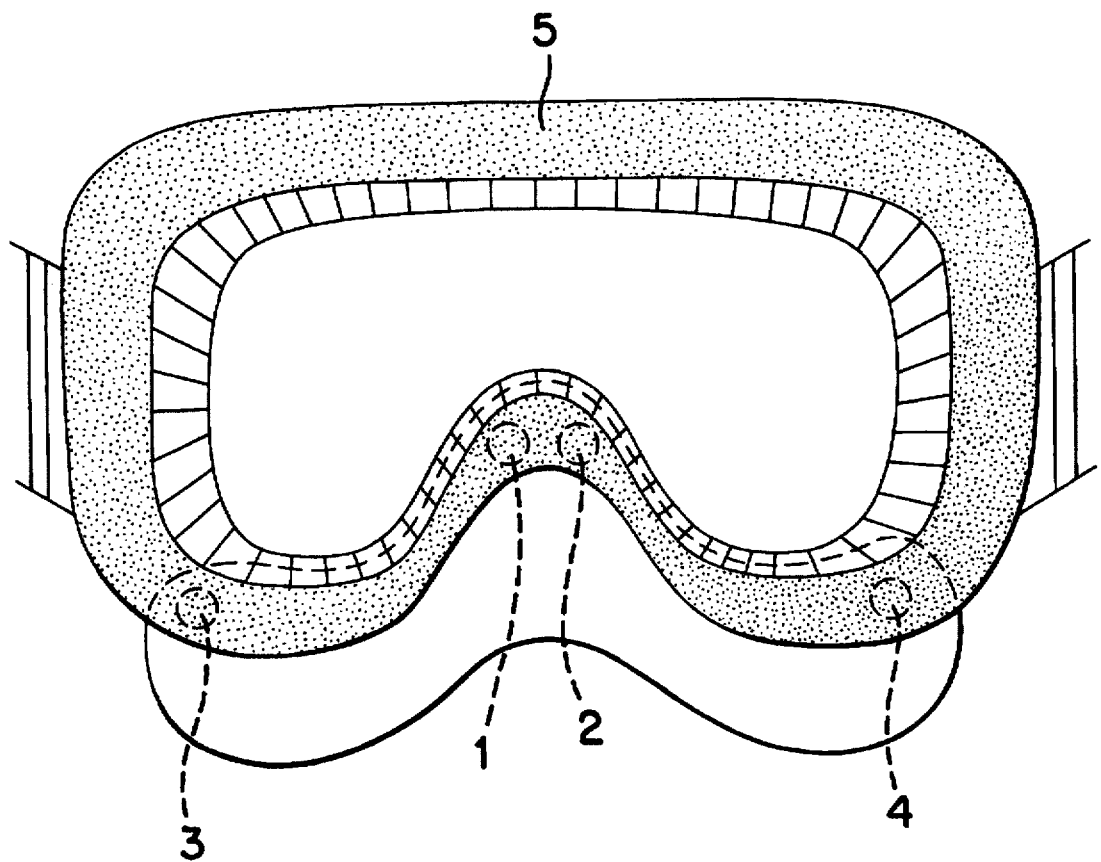
FIG. 3 is a frontal view of the attachment of the invention to a pair of ski goggles.

A frontal view of the invention attached to ski goggles is illustrated in FIG. 3. The hook fasteners 1 and 2 are attached to the foam 5 on the inside of the goggles on either side of the upper portion of the bridge of the nose. The hook fasteners 3 and 4 are attached to the foam 5 on the inside of the goggles along the upper curve of the cheek area. The sewn over edge is not illustrated in FIG. 3.

We claim:

1. A nose and cheek warmer and protector comprising:

(a) a panel having a perimeter including a top edge which extends over the bridge of a wearer's nose and across the wearer's skin beneath the eyes, two side edges which lie against the cheeks on each side of the wearer's face, and a lower edge which lies across an upper cheek area and across a lower tip of the nose above the nostrils of the wearer, said panel lying against the wearer's skin without covering or surrounding the eyes, nostrils, or mouth, (b) said panel being made of an opaque, thermally insulating, and absorptive material which helps to maintain skin warmth, absorb moisture, and prevent the direct transmission of sunlight or wind to the skin surface, (c) an attachment means adjacent said top edge for securing the protector to a foam lining of ski goggles, allowing molding of the panel to the shape of the face and nose of the wearer, and (d) stitching along the perimeter and over said edges which helps to maintain the integrity of the overall panel shape, reducing fraying during usage and laundering.

* * * * *